(12) United States Patent
Kim et al.

(10) Patent No.: US 11,752,482 B2
(45) Date of Patent: Sep. 12, 2023

(54) RESTRUCTURED HYDROGEL AND PREPARING METHOD OF THE SAME

(71) Applicant: Research & Business Foundation Sungkyunkwan University, Suwon-si (KR)

(72) Inventors: Jae Yun Kim, Suwon-si (KR); Donghwan Ji, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 237 days.

(21) Appl. No.: 17/168,490

(22) Filed: Feb. 5, 2021

(65) Prior Publication Data
US 2021/0260556 A1    Aug. 26, 2021

(30) Foreign Application Priority Data

Feb. 21, 2020 (KR) .................. 10-2020-0021805
Jan. 13, 2021 (KR) .................. 10-2021-0004440

(51) Int. Cl.
| | |
|---|---|
| *B01J 13/00* | (2006.01) |
| *C08J 3/075* | (2006.01) |
| *C08K 7/18* | (2006.01) |
| *C08J 3/24* | (2006.01) |
| *A61L 31/14* | (2006.01) |
| *C08K 3/16* | (2006.01) |
| *C08K 3/22* | (2006.01) |

(Continued)

(52) U.S. Cl.
CPC ........... *B01J 13/0065* (2013.01); *A61L 27/52* (2013.01); *A61L 31/145* (2013.01); *B01J 13/0069* (2013.01); *C08J 3/075* (2013.01); *C08J 3/24* (2013.01); *C08K 3/06* (2013.01); *C08K 3/22* (2013.01); *C08K 7/18* (2013.01); *A61L 2430/10* (2013.01); *A61L 2430/30* (2013.01); *C08J 2333/26* (2013.01); *C08J 2405/04* (2013.01); *C08K 2003/2227* (2013.01)

(58) Field of Classification Search
CPC ............... A61L 27/52; C08J 3/24; C08K 7/18
See application file for complete search history.

(56) References Cited

U.S. PATENT DOCUMENTS

| | | | |
|---|---|---|---|
| 6,264,695 B1 | 7/2001 | Stoy | |
| 9,394,384 B2 * | 7/2016 | Muratoglu | ............. C08L 29/04 |
| 2015/0182660 A1* | 7/2015 | Nazhat | ................... A61L 27/54 |
| | | | 425/398 |

FOREIGN PATENT DOCUMENTS

| | | | | |
|---|---|---|---|---|
| JP | 2002053629 A | * | 2/2002 | ............. A61L 15/60 |
| KR | 101725645 B1 | * | 4/2017 | |
| KR | 10-1881249 B2 | * | 7/2018 | |

(Continued)

OTHER PUBLICATIONS

Kim (Bioinspired Structural Composite Hydrogels with a Combination of High Strength, Stiffness, and Toughness, Adv. Funct. Matr. 2021, 31, 8 pages).*

(Continued)

*Primary Examiner* — Brieann R Johnston
(74) *Attorney, Agent, or Firm* — NSIP Law

(57) ABSTRACT

The present disclosure relates to a method for preparing a restructured hydrogel, including forming a hydrogel containing a first polymer, unidirectionally shrinking and dehydrating the hydrogel, and additionally cross-linking and rehydrating the dehydrated hydrogel.

16 Claims, 18 Drawing Sheets

(51) Int. Cl.
    *A61L 27/52*    (2006.01)
    *C08K 3/06*    (2006.01)

(56) References Cited

FOREIGN PATENT DOCUMENTS

| KR | 10-2018-0113818 A | 10/2018 | | |
|----|----|----|----|----|
| WO | WO-0168156 A1 | * | 9/2001 | ............ A61L 15/18 |
| WO | WO-2016178586 A2 | * | 11/2016 | |
| WO | WO-2019164931 A1 | * | 8/2019 | ........... A61K 9/0014 |

OTHER PUBLICATIONS

Machine translation of KR 101881249 (2018, 8 pages).*
Machine translation of KR 101725645 (2017, 8 pages).*
Machine translation of JP 2002053629 (2002, 18 pages).*
Machine translation of WO 0168156 (2001, 19 pages).*
Choi (Anisotropic Hybrid Hydrogels with Superior Mechanical Properties Reminiscent of Tendons or Ligaments, Adv. Funct. Mater. 2019, 29, 9 pages).*
Eveflow (Sodium alginate and applications: a review, Eveflow, Aug. 2020, 4 pages).*
Amornwachirabodee, Kittima, et al. "Uniaxial Swelling in LC Hydrogels Formed by Two-Step Cross-Linking." Macromolecules 48.23 (2015): (7 pages in English).

* cited by examiner

[FIG. 1]
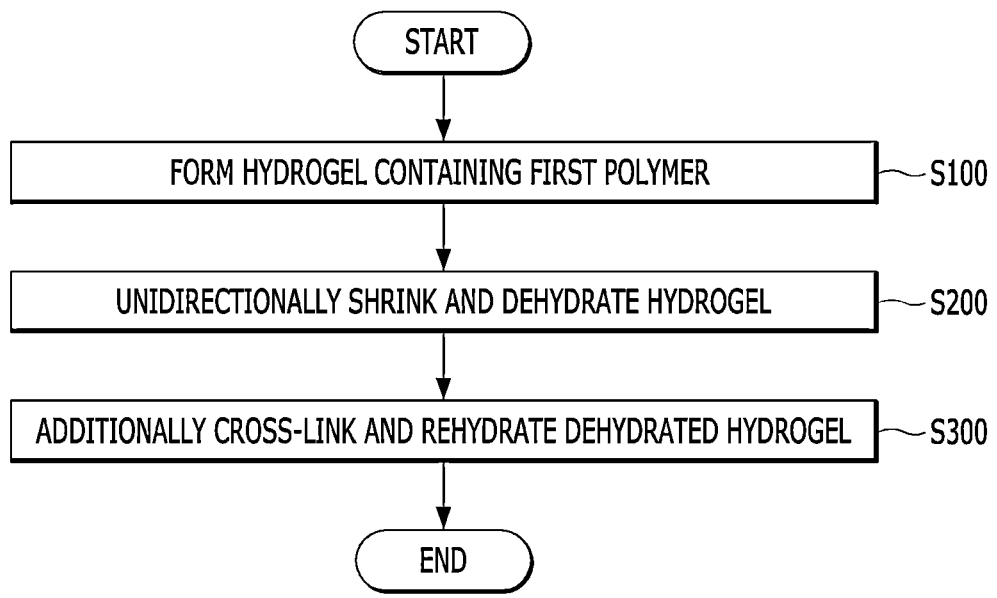

[FIG. 2]
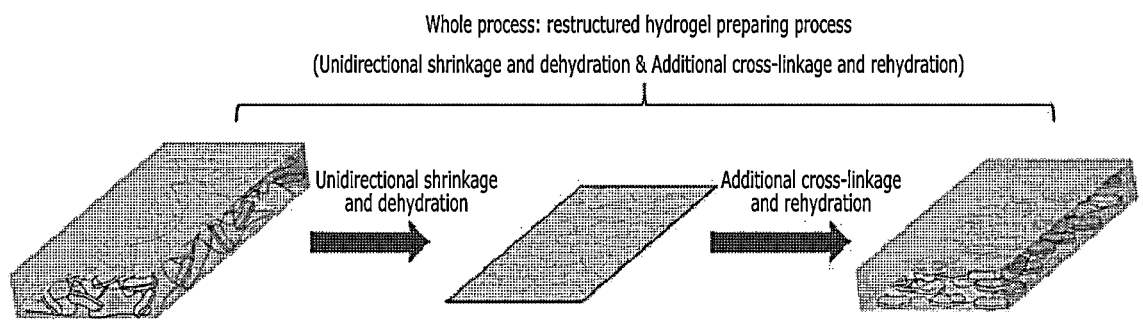

[FIG. 3]
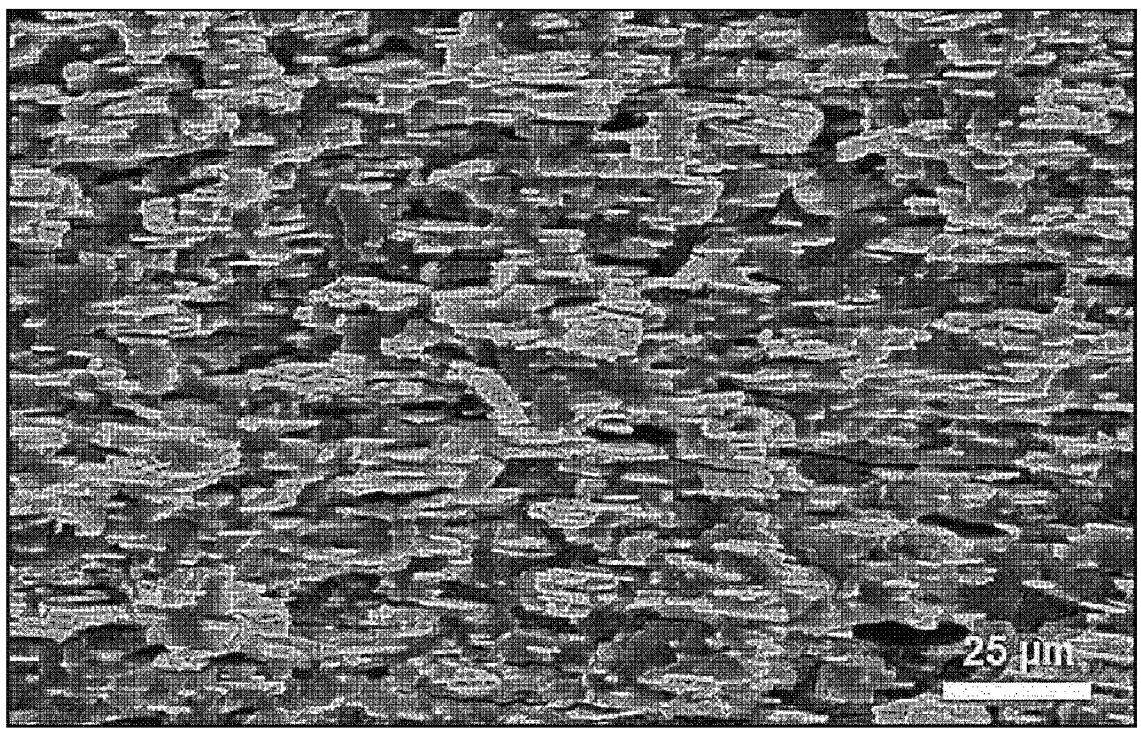

[FIG. 4]
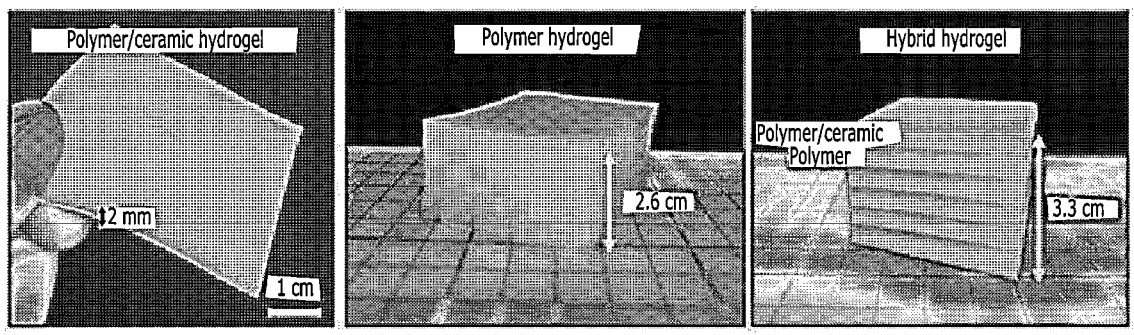

[FIG. 5]
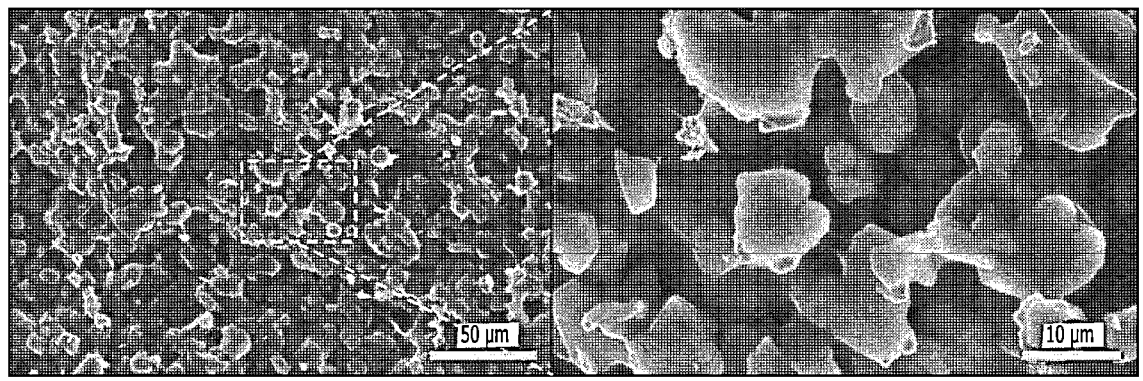

[FIG. 6]
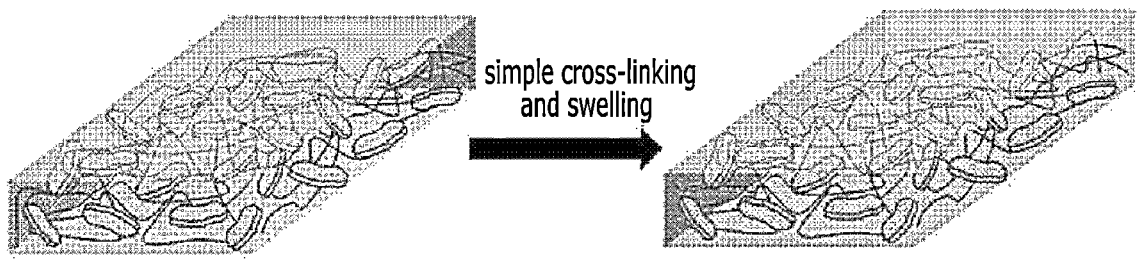

[FIG. 7]
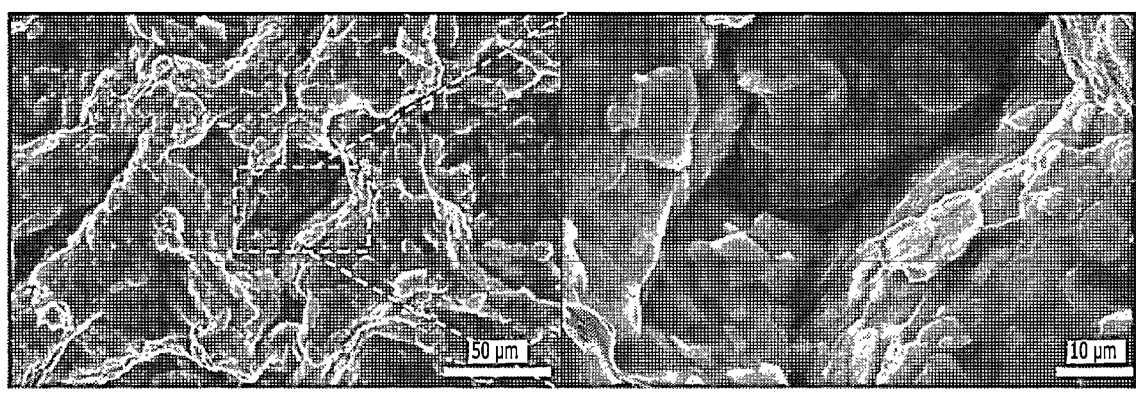

[FIG. 8]
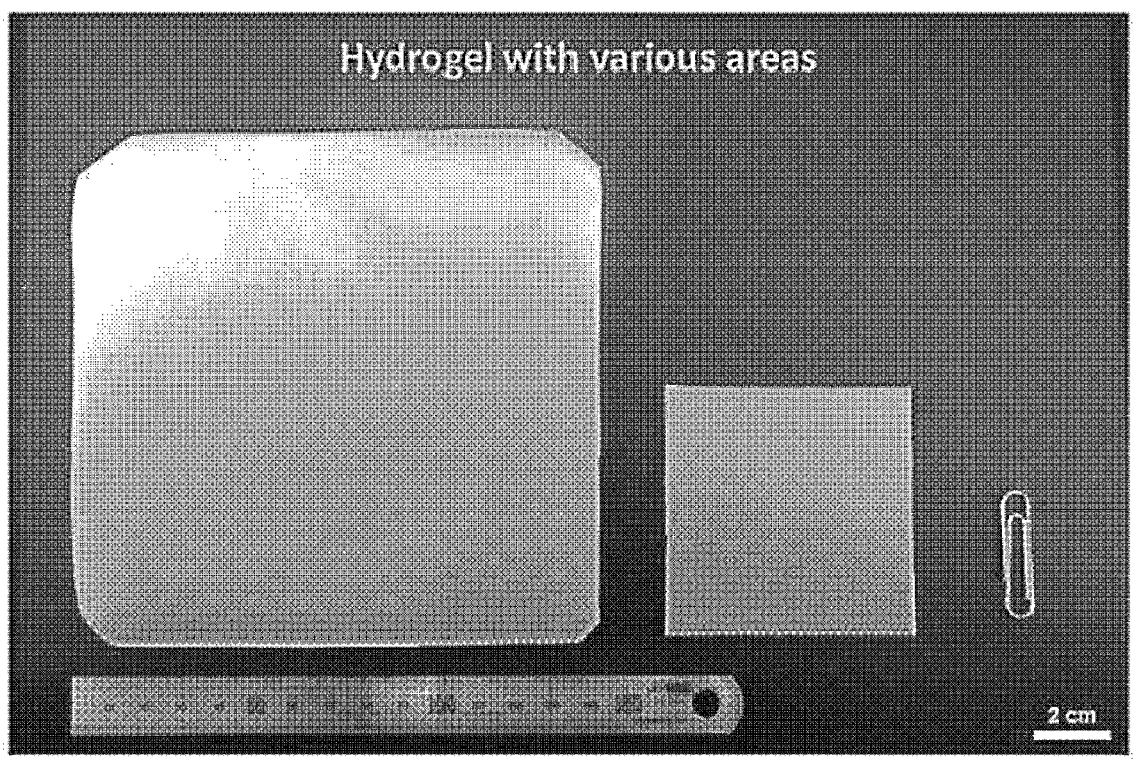

[FIG. 9]
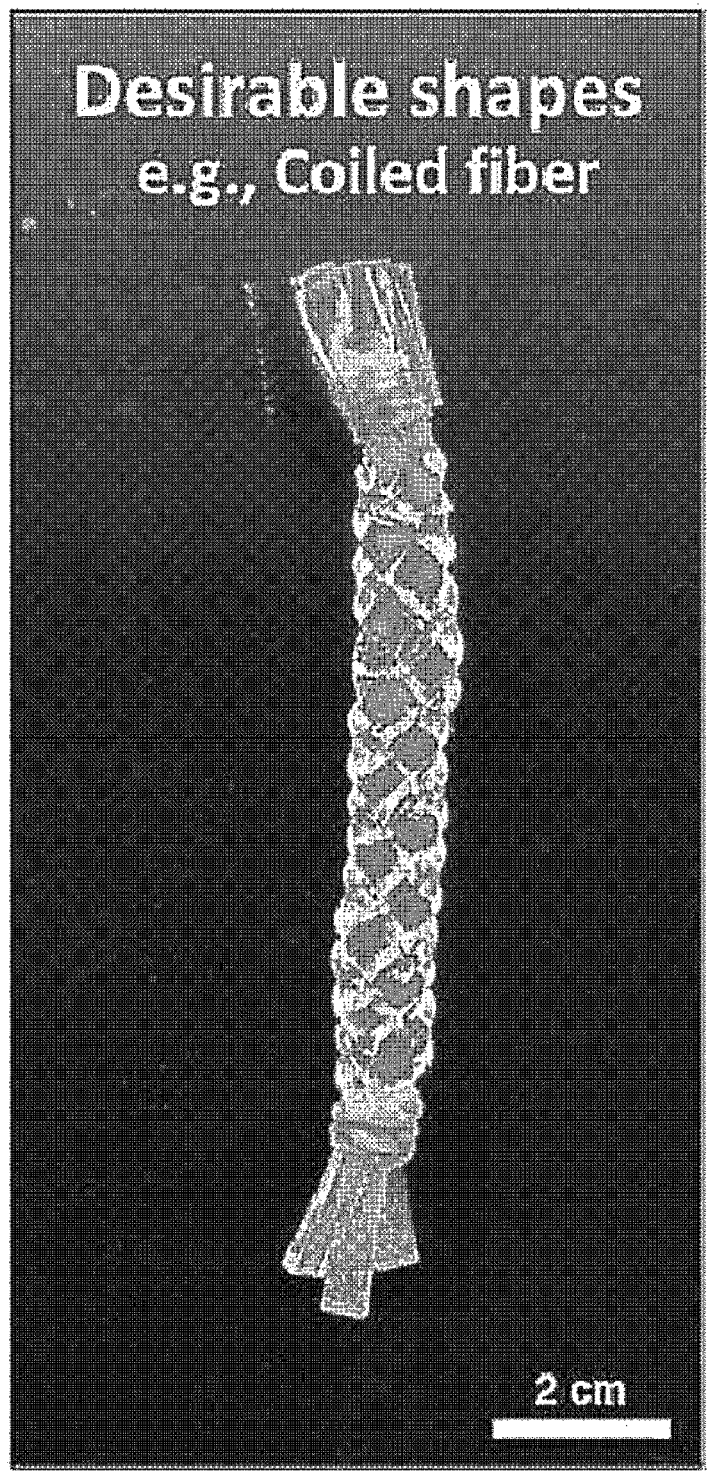

[FIG. 10]
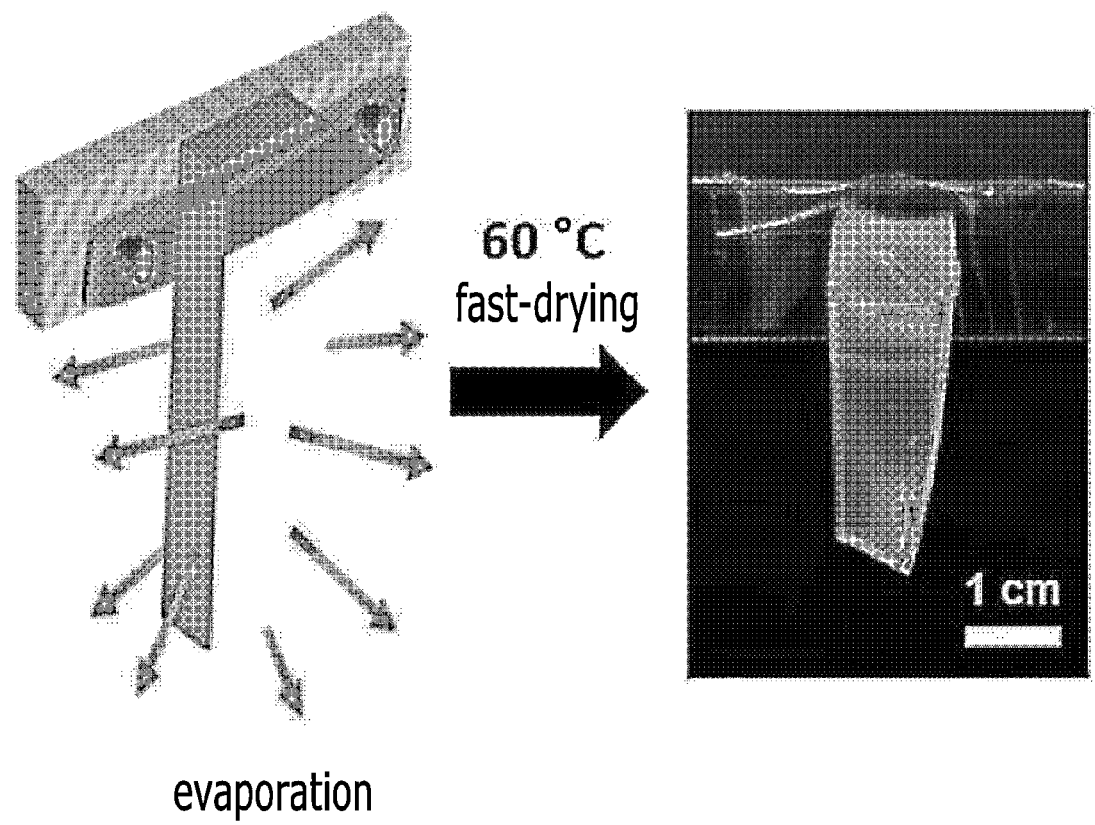

[FIG. 11]
Comparative example 2-1
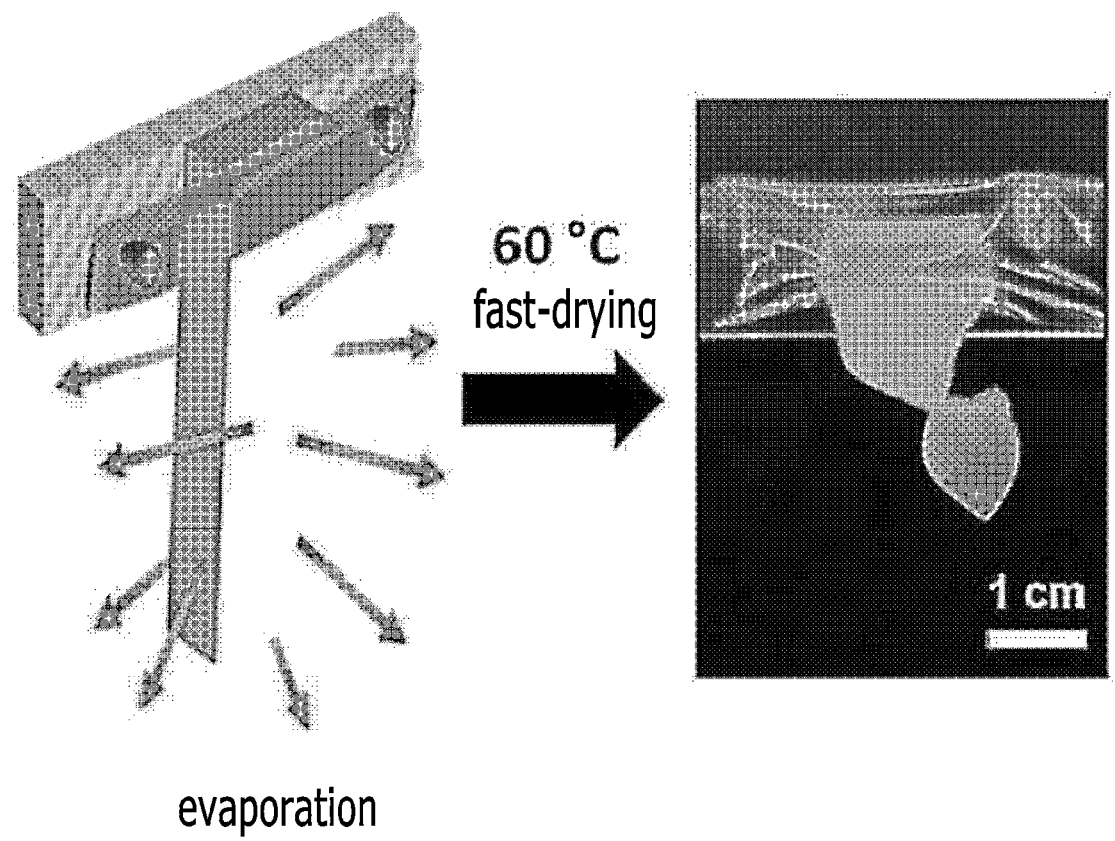
evaporation

[FIG. 12]
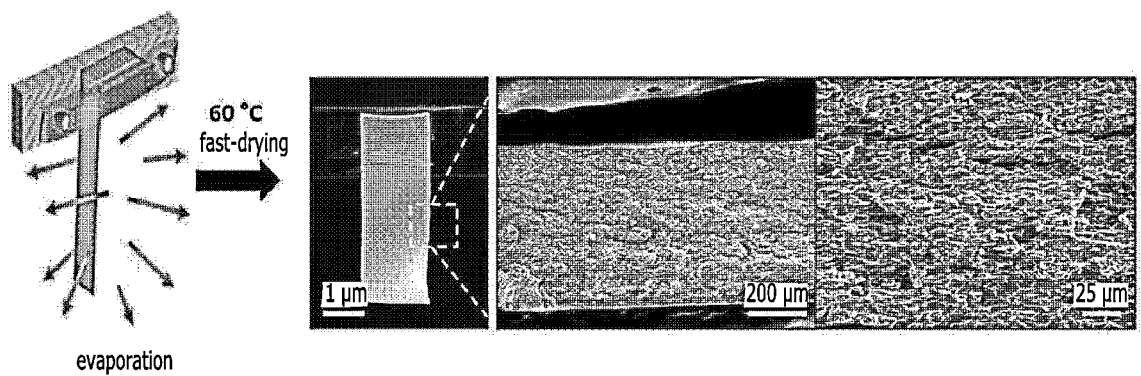

[FIG. 13]
Comparative example 2-4
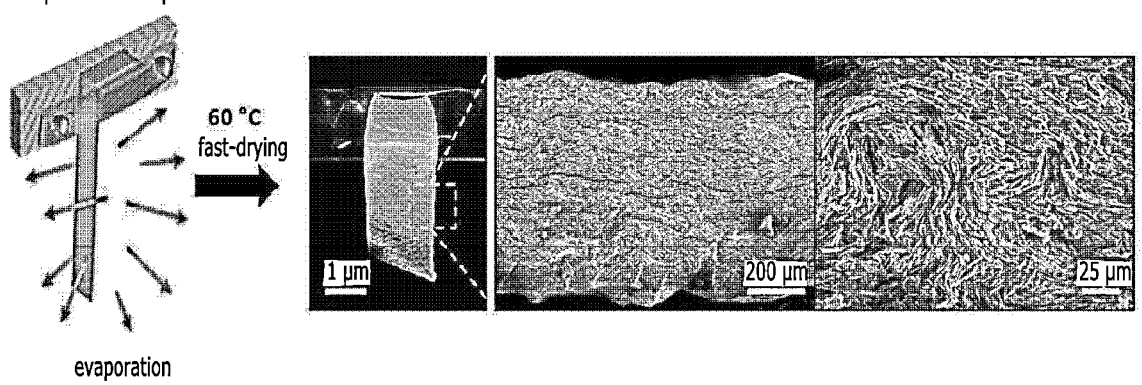

[FIG. 14]
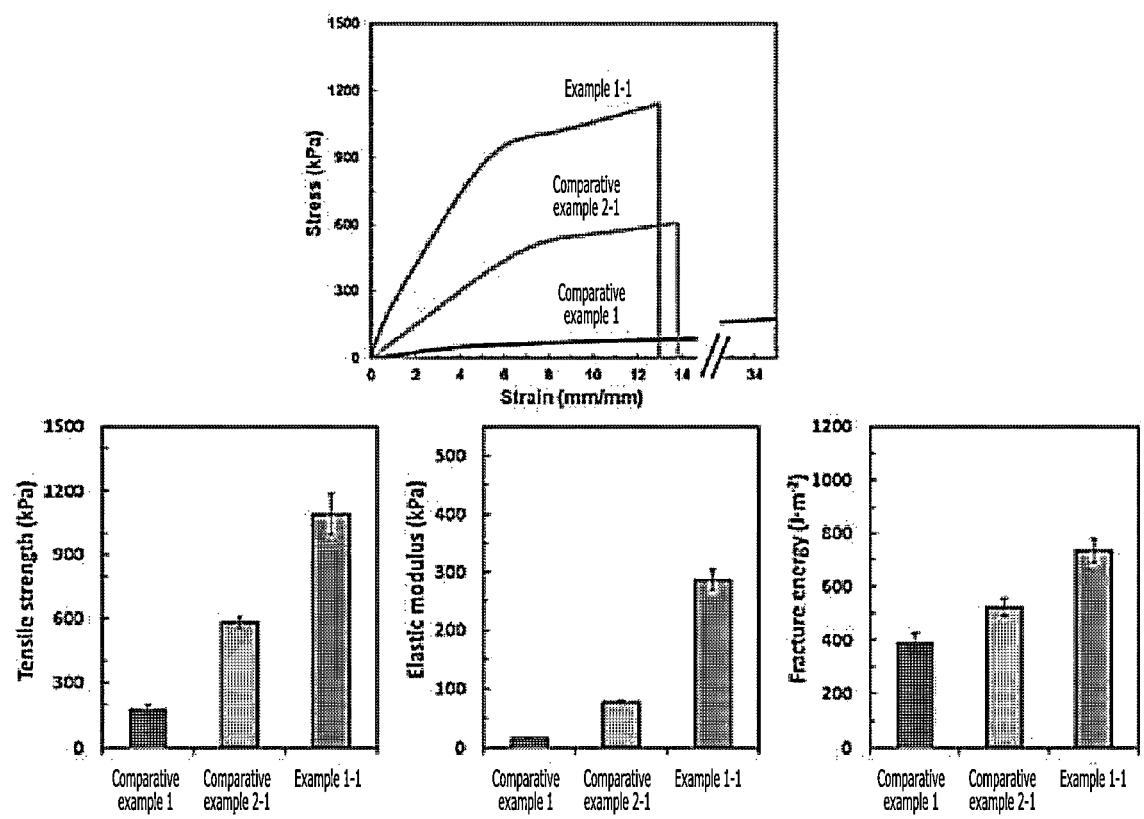

[FIG. 15]
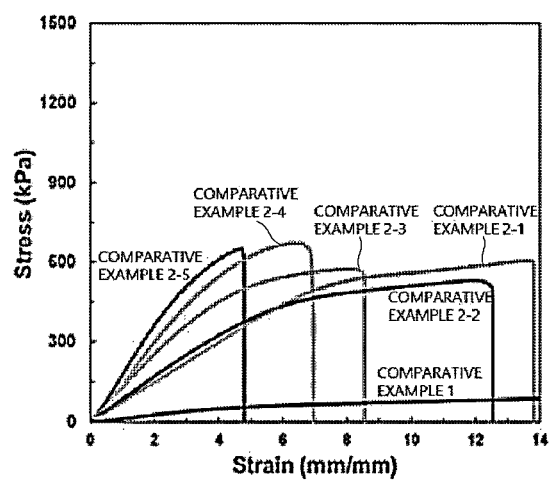 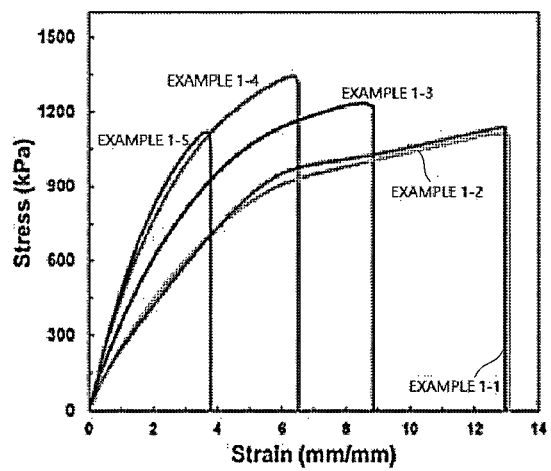

[FIG. 16]
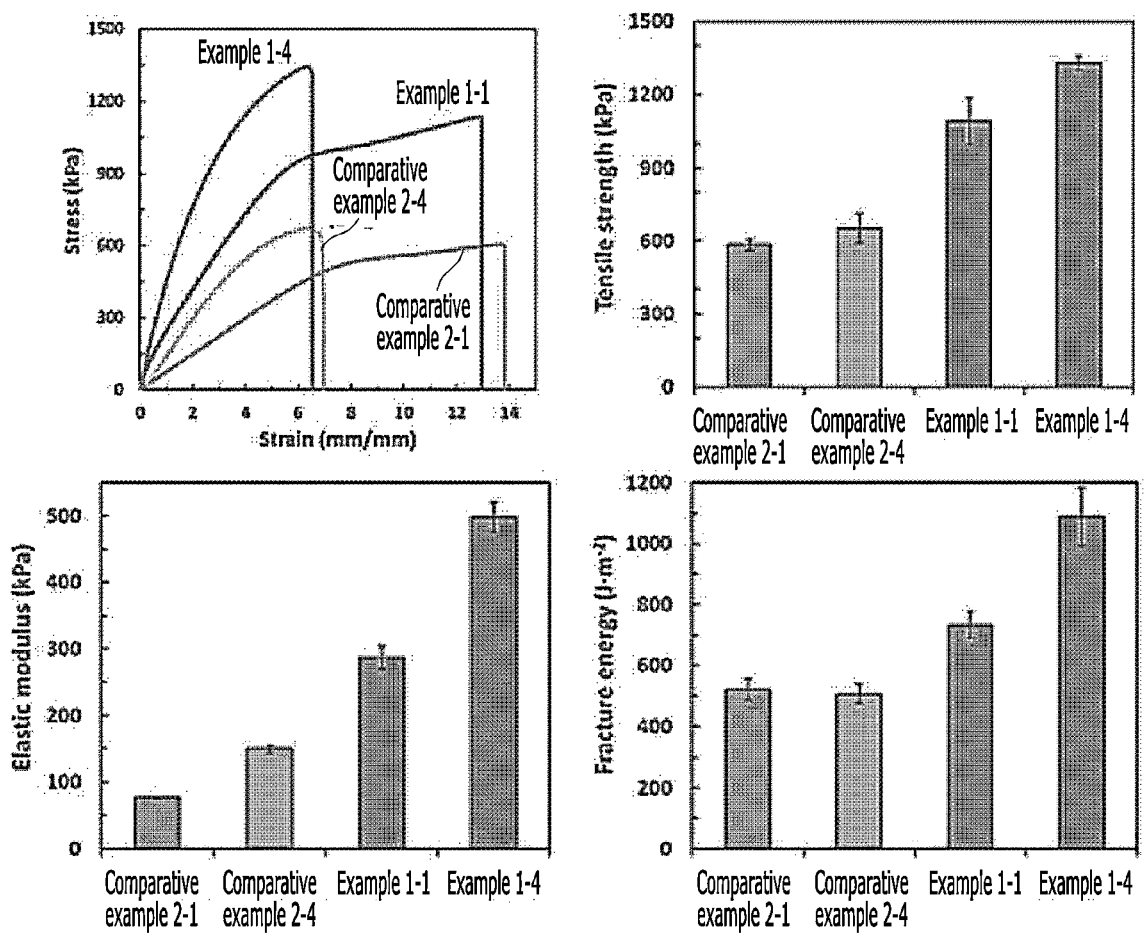

[FIG. 17]
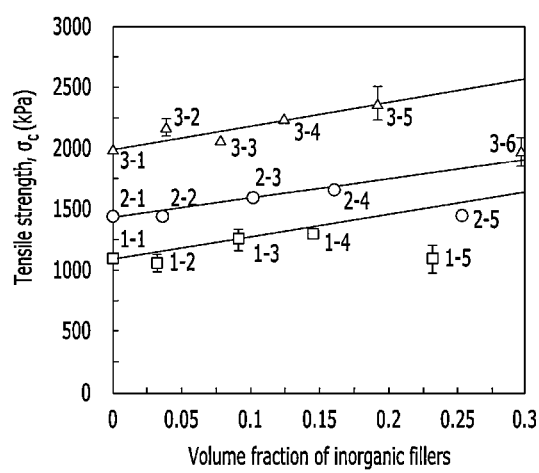
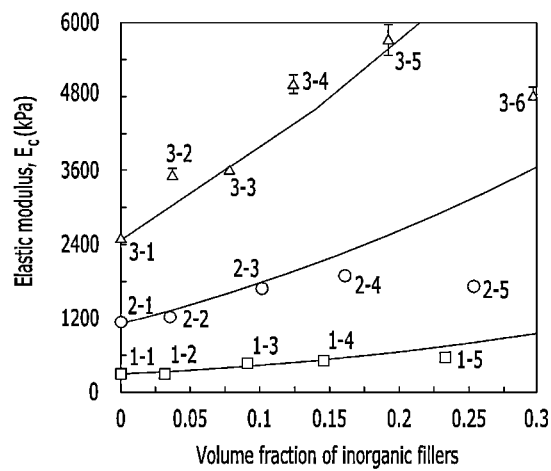

[FIG. 18]
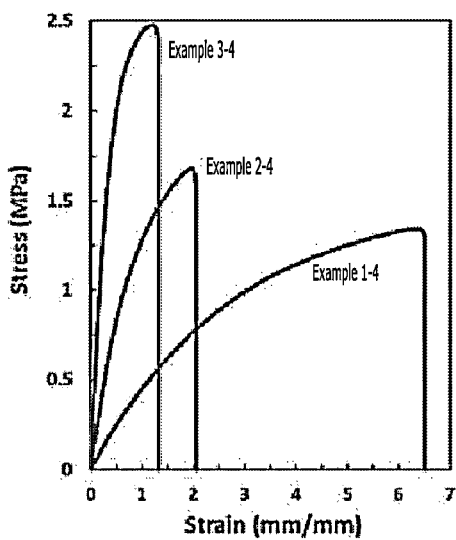
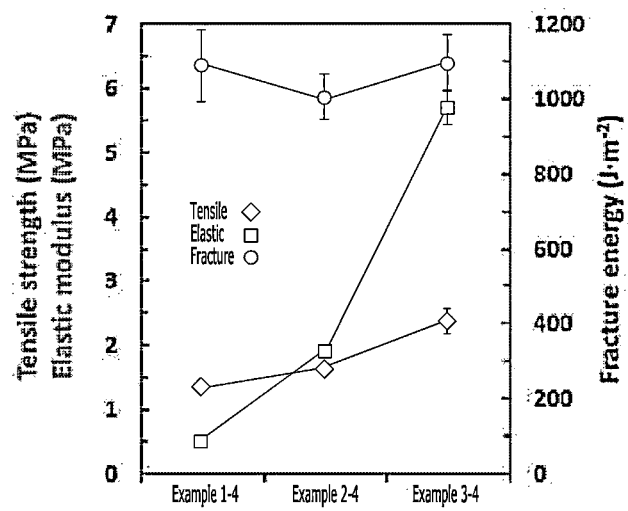

RESTRUCTURED HYDROGEL AND PREPARING METHOD OF THE SAME

CROSS-REFERENCE TO RELATED APPLICATION

This application claims the benefit under 35 U.S.C. 119(a) of Korean Patent Application No. 10-2020-0021805 filed on Feb. 21, 2020 and Korean Patent Application No. 10-2021-0004440 filed on Jan. 13, 2021, in the Korean Intellectual Property Office, the entire disclosure of which is incorporated herein by reference for all purposes.

BACKGROUND

1. Field

The present disclosure relates to a restructured hydrogel and a preparing method of the same.

2. Description of the Background

A hydrogel is a three-dimensional cross-linked hydrophilic polymer network that is formed by physical bonding such as hydrogen bonding, van der Waals force, hydrophobic interactions, and crystallization of polymers, and/or chemical bonding such as covalent bonding. A hydrogel does not dissolve in an aquatic environment and can contain a great amount of water. Also, a hydrogel can be formed of various hydrophilic polymers, and thus have various chemical compositions and properties.

As can be seen from successful applications to a peritoneum and various parts in a body, the hydrogel is highly biocompatible due to its high water content and physicochemical similarity with extracellular matrices. A hydrogel can be used in various ways due to its properties and has received a lot of attention as one of the attractive materials, particularly for medical and pharmacological applications.

Additionally, a hydrogel has high water content and softness similar to those of biological tissues, and, thus, there have been attempts to substitute a hydrogel for artificial muscles, ligaments, tendons and the like, and to use the hydrogel as a base material to be combined with hard electronic devices for development of soft bioelectronic device materials. Here, smaller differences in mechanical properties between a hydrogel and biological tissues are better. This is because discomfort can be reduced while the body moves, and efficiency in interactions between electronic devices and biological tissues can be maximized.

However, a conventional hydrogel has remarkably lower mechanical properties such as strength, stiffness, and toughness than actual biological tissues, causes incompatibility with actual biological tissues, and thus can be easily fractured by an external impact. Accordingly, a study for enhancing the mechanical properties of a hydrogel is needed.

Until recently there have been two main methods for enhancing mechanical properties of a hydrogel. The first method is to increase an alignment and a density of a polymer by one-way direction similar to a drawing process in fiber production. The second method is to add spherical particles or fiber with proper length as inorganic reinforced plastic.

However, in general, a hydrogel, unlike a common fiber that has uniform elasticity, is partly elastic. The partial elasticity of a hydrogel causes an uneven distribution of properties and makes it difficult to produce a hydrogel in large area. In general, when a reinforced plastic is added, the reinforced plastic is introduced by simple mixing, and thus, enhancement of properties is limited, and sometimes it even requires a rather fastidious top-down process.

Korean Patent Laid-open Publication No. 10-2018-0113818 relates to a method for preparing a transparent silica hydrogel and discloses a method for enhancing mechanical strength of a hydrogel by adding water glass, but does not disclose a method to improve other mechanical properties such as stiffness and fracture toughness. Therefore, the method cannot sufficiently solve the above-described problem.

Accordingly, a method for preparing a hydrogel that can easily produce the hydrogel in larger area, can be universally applied, and can effectively enhance mechanical properties, is required. In addition, a hydrogel with excellent mechanical properties is required.

The above information is presented as background information only to assist with an understanding of the present disclosure. No determination has been made, and no assertion is made, as to whether any of the above might be applicable as prior art with regard to the disclosure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

According to a first aspect of the present disclosure, there is provided a method for preparing a restructured hydrogel, including: forming a hydrogel containing a first polymer; unidirectionally shrinking and dehydrating the hydrogel; and additionally cross-linking and rehydrating the dehydrated hydrogel.

According to an embodiment of the present disclosure, the first polymer may be formed through cross-linking of ionic bonds and/or covalent bonds, but may not be limited thereto.

According to an embodiment of the present disclosure, the first polymer may include a member selected from the group consisting of alginate (ALG), polyethylene glycol (PEG), chitosan, gelatin, polyacrylic acid (PAA), polyacrylamide (PAM), polyNIPAM (PNIPAM), agar, poly(2-acrylamido-2-methylpropane sulfonic acid) (PAMPS) and combinations thereof, but may not be limited thereto.

According to an embodiment of the present disclosure, the additional cross-linking and rehydration may be performed by impregnating the dehydrated hydrogel in a cross-linker solution, but may not be limited thereto.

According to an embodiment of the present disclosure, the cross-linker solution may contain an ion selected from the group consisting of $Ba^{2+}$, $Ca^{2+}$, $Al^{3+}$, $Fe^{3+}$, $Fe^{2+}$, $Mg^{2+}$, $Cu^{2+}$, $Sr^{2+}$, $Co^{2+}$, $Mn^{2+}$, $Ni^{2+}$, $Sn^{2+}$, $Zn^{2+}$, $Ga^{3+}$, $Ti^{3+}$, $Na^{+}$, $K^{+}$, $Li^{+}$ and combinations thereof, but may not be limited thereto.

According to an embodiment of the present disclosure, the cross-linker solution may contain a material selected from the group consisting of N,N''-methylenebisacrylamide (MBAA), N,N-dimethylacrylamide (DMA), glutaraldehyde (GA), N,N''-bis(acryloyl)cystamine (BAC), N,N''-diallyl tartar diamide (DATD), ethylene diacrylate (EDIA) and combinations thereof, but may not be limited thereto.

According to an embodiment of the present disclosure, the process of forming the hydrogel may include: hydrogelating the mixture solution by adding a cross-linker to a monomer of the first polymer, but may not be limited thereto.

According to an embodiment of the present disclosure, the mixture solution may further contain inorganic particles, but may not be limited thereto.

According to an embodiment of the present disclosure, the inorganic particles may include a member selected from the group consisting of aluminum oxide ($Al_2O_3$), boron nitride (BN), mica, illite, magnesium hydroxide (Mg(OH)2), aluminum nitride (AlN), boron carbide ($B_4C$) and combinations thereof, but may not be limited thereto.

According to an embodiment of the present disclosure, the first polymer and the inorganic particles may form a layered structure, but may not be limited thereto.

According to an embodiment of the present disclosure, the inorganic particles may be coated with second polymer, but may not be limited thereto.

According to an embodiment of the present disclosure, the second polymer may include a member selected from the group consisting of polyethylene (PE), polyvinyl chloride (PVC), polypropylene (PP), polyvinylpyrrolidone (PVP), polyacrylic acid (PAA), polyvinyl acetate (PVA), polystyrene (PS), polyurethane (PU) and combinations thereof, but may not be limited thereto.

According to an embodiment of the present disclosure, the shrinkage and dehydration may be performed at a temperature from 10° C. to 100° C., but may not be limited thereto.

Also, according to a second aspect of the present disclosure, there is provided a restructured hydrogel, including a restructured polymer network and inorganic particles, and the restructured polymer network is aligned unidirectionally, and the restructured polymer network and the inorganic particles form a layered structure.

Also, according to a third aspect of the present disclosure there is provided a bioelectronic device containing a restructured hydrogel according to the second aspect of the present disclosure.

Other features and aspects will be apparent from the following detailed description, the drawings, and the claims.

BRIEF DESCRIPTION OF THE DRAWINGS

In the detailed description that follows, embodiments are described as illustrations only since various changes and modifications will become apparent to a person with ordinary skill in the art from the following detailed description. The use of the same reference numbers in different figures indicates similar or identical items.

FIG. 1 is a flowchart showing the method for preparing a restructured hydrogel according to an embodiment of the present disclosure.

FIG. 2 is a conceptual diagram showing the method for preparing a restructured hydrogel according to an embodiment of the present disclosure.

FIG. 3 is an electron micrograph of the cross section of the hydrogel containing inorganic particles after unidirectional shrinkage and dehydration in the method for preparing the hydrogel according to an example of the present disclosure.

FIG. 4 is an image of the restructured hydrogel according to an example of the present disclosure.

FIG. 5 is an electron micrograph of the top surface of the hydrogel of FIG. 3, which has been additionally cross-linked, rehydrated, and then lyophilized.

FIG. 6 is a schematic diagram showing the method for preparing the hydrogel according to a comparative example of the present disclosure.

FIG. 7 is an electron micrograph of the top surface of the hydrogel prepared according to a comparative example of the present disclosure, which has been subsequently lyophilized.

FIG. 8 is a photograph of the large-area hydrogel according to an example of the present disclosure.

FIG. 9 is a photograph of the hydrogel according to an example of the present disclosure.

FIG. 10 is a photograph of the restructured hydrogel according to an example of the present disclosure, which has been subsequently fast-dried.

FIG. 11 is a photograph of the hydrogel according to a comparative example of the present disclosure, which has been subsequently fast-dried.

FIG. 12 shows a photograph of the restructured hydrogel containing inorganic particles according to an example of the present disclosure, which has been subsequently fast-dried, and an electron micrograph of a cross section of the sample obtained from the restructured hydrogel.

FIG. 13 shows a photograph of the hydrogel according to a comparative example of the present disclosure, which has been subsequently fast-dried, and an electron micrograph of a cross section of the sample obtained from the hydrogel.

FIG. 14 shows the test results of mechanical properties in tension tests of the hydrogels according to an example and a comparative example of the present disclosure.

FIG. 15 shows the test results of mechanical properties in tension tests of the hydrogels according to an example and a comparative example of the present disclosure.

FIG. 16 shows the test results of mechanical properties in tension tests of the hydrogel according to an example and a comparative example of the present disclosure.

FIG. 17 shows the test results of mechanical properties in a tension test of the hydrogel according to an example of the present disclosure.

FIG. 18 shows the test results of mechanical properties in a tension test of the hydrogel according to an example of the present disclosure.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of this disclosure. For example, the sequences of operations described herein are merely examples, and are not limited to those set forth herein, but may be changed as will be apparent after an understanding of this disclosure, with the exception of operations necessarily occurring in a certain order. Also, descriptions of features that are known in the art may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of this disclosure. Hereinafter, while embodiments of the present disclosure will be described in detail with reference to the accompanying drawings, it is noted that examples are not limited to the same.

Throughout the whole disclosure, the term "connected to" or "coupled to" that is used to designate a connection or coupling of one element to another element includes both a case that an element is "directly connected or coupled to" another element and a case that an element is "electronically connected or coupled to" another element via still another element.

Throughout the whole disclosure, the terms "on", "above", "on an upper end", "below", "under", and "on a lower end" that are used to designate a position of one element with respect to another element include both a case that the one element is adjacent to the other element and a case that any other element exists between these two elements.

Further, throughout the whole disclosure, the term "comprises or includes" and/or "comprising or including" used in the document means that one or more other components, steps, operation and/or existence or addition of elements are not excluded in addition to the described components, steps, operation and/or elements unless context dictates otherwise.

Throughout the whole disclosure, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Throughout the whole disclosure, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the whole disclosure, a phrase in the form "A and/or B" means "A or B, or A and B".

Hereinafter, the method for preparing restructured hydrogel according to the present disclosure, the restructured hydrogel produced by the method, and the bioelectronic device materials including the same will be described in detail with reference to the embodiments, examples, and drawings. However, the present disclosure is not limited to these embodiments, examples and drawings.

In view of the foregoing, the present disclosure provides the method to produce the restructured hydrogel having excellent mechanical properties by orientation of polymers network and inorganic particles. Furthermore, the present disclosure provides the restructured hydrogel prepared by the method.

In the method for preparing the restructured hydrogel according to the present disclosure, a density of polymer contained in the hydrogel increases, inorganic particles such as reinforced plastic are formed into a layered structure, and a bonding force between the polymer and the inorganic particles increases. The restructured hydrogel prepared by the method has excellent mechanical properties, such as strength, stiffness, fracture toughness, and has excellent anisotropic thermal conductivity.

In the method for preparing the restructured hydrogel according to the present disclosure, interactions between the polymer and the inorganic particles increase, and, thus, the mechanical properties of the hydrogel can be effectively enhanced.

According to the method for preparing the restructured hydrogel of the present disclosure, the hydrogel can be produced in large area, and the method can be universally applied.

The restructured hydrogel according to the present disclosure can be applied to a wide variety of fields due to the above-described features. For example, the restructured hydrogel according to the present disclosure can be variously applied to artificial muscles, artificial ligaments, tendons, bioelectronic devices, gel-type electrolyte such as separator, and the like.

In particular, compared with a conventional hydrogel, the restructured hydrogel of the present disclosure has enhanced mechanical strength, stiffness, and fracture toughness, and thus can also be used in applications, where great amount of load is present such as in muscles, tendons or gel-type electrolyte such as separator.

The effects to be achieved by the present disclosure are not limited to the above-described effects. There may be other effects to be achieved by the present disclosure.

According to a first aspect of the present disclosure, there is provided a method for preparing a restructured hydrogel, including: forming a hydrogel containing a first polymer; unidirectionally shrinking and dehydrating the hydrogel; and additionally cross-linking and rehydrating the dehydrated hydrogel.

Hereinafter, the method for preparing restructured hydrogel according to the present disclosure is described with reference to FIG. 1 and FIG. 2.

FIG. 1 is a flowchart showing a method for preparing a restructured hydrogel according to an embodiment of the present disclosure.

FIG. 2 is a conceptual diagram showing the method for preparing a restructured hydrogel according to an embodiment of the present disclosure.

First, a hydrogel containing a first polymer is formed (S100).

According to an embodiment of the present disclosure, the first polymer may be formed through cross-linking by ionic bonds and/or covalent bonds, but may not be limited thereto.

According to an embodiment of the present disclosure, the first polymer may include a member selected from the group consisting of alginate (ALG), polyethylene glycol (PEG), chitosan, gelatin, polyacrylic acid (PAA), polyacrylamide (PAM), polyNIPAM (PNIPAM), agar, poly(2-acrylamido-2-methylpropane sulfonic acid (PAMPS), and combinations thereof, but may not be limited thereto.

The first polymer may contain two or more kinds of polymers and have the enhanced mechanical properties compared with each of the polymers contained therein. For example, the first polymer may be formed by bonding polyacrylamide and alginate and may have the enhanced mechanical properties compared with each of polyacrylamide and alginate and thus is not easily fractured by external impact.

According to an embodiment of the present disclosure, the process of forming the hydrogel may include hydrogelating a mixture solution by adding a cross-linker to a monomer of the first polymer, but may not be limited thereto.

Specifically, the first polymer may be formed by polymerizing and cross-linking the monomer. The monomer may include a monomer that forms an ionic bond or a monomer that forms a covalent bond.

According to an embodiment of the present disclosure, the cross-linker may contain an ion selected from the group consisting of $Ba^{2+}$, $Ca^{2+}$, $Al^{3+}$, $Fe^{3+}$, $Fe^{2+}$, $Mg^{2+}$, $Cu^{2+}$, $Sr^{2+}$, $Co^{2+}$, $Mn^{2+}$, $Ni^{2+}$, $Sn^{2+}$, $Zn^{2+}$, $Ga^{3+}$, $Ti^{3+}$, $Na^+$, $K^+$, $Li^+$ and combinations thereof, but may not be limited thereto. The cross-linker may induce cross-linking by ionic bonds.

According to an embodiment of the present disclosure, the cross-linker may contain a material selected from the group consisting of N,N''-methylenebisacrylamide (MBAA), N,N-dimethylacrylamide (DMA), glutaraldehyde (GA), N,N''-bis(acryloyl)cystamine (BAC), N,N''-diallyl tartar diamide (DATD), ethylene diacrylate (EDIA) and combinations thereof, but may not be limited thereto. The cross-linker may induce cross-linking by covalent bonds.

The mechanical properties of the restructured hydrogel can be regulated by regulating the kind or amount of the cross-linker. In this regard, as the cross-linker is more strongly bonded to the polymer or the first polymer contains the cross-linker at a higher ratio, the first polymer has a higher density. Therefore, the mechanical properties of the restructured hydrogel according to the present disclosure can be regulated.

According to an embodiment of the present disclosure, the mixture solution may further contain inorganic particles, but may not be limited thereto.

According to an embodiment of the present disclosure, the inorganic particles may include a member selected from the group consisting of aluminum oxide ($Al_2O_3$), boron nitride (BN), mica, illite, magnesium hydroxide ($Mg(OH)_2$), aluminum nitride (AlN), boron carbide ($B_4C$) and combinations thereof, but may not be limited thereto.

The inorganic particles have thermal conductivity. The restructured hydrogel according to the present disclosure contains inorganic particles and thus can enhance thermal conductivity.

According to an embodiment of the present disclosure, the first polymer and the inorganic particles may form a layered structure, but may not be limited thereto.

The layered structure can achieve a more remarkable enhancement of mechanical properties than a structure in which the inorganic particles are chaotically arranged. Specifically, the inorganic particles are broad and flat with small thickness; thus have excellent mechanical strength and stiffness. The restructured hydrogel according to the present disclosure contains the inorganic particles in a uniformly layered structure and thus has excellent mechanical strength, stiffness, fracture toughness. The mechanical properties of the restructured hydrogel can be regulated by regulating the amount of the inorganic particles.

According to an embodiment of the present disclosure, the inorganic particles may be coated with a second polymer, but may not be limited thereto.

Since the second polymer is coated on the inorganic particles, the interactions between the first polymer and the inorganic particles can increase, and, thus, the mechanical properties of the restructured hydrogel according to the present disclosure can be effectively enhanced.

A polymer that can be physically or chemically bonded to the first polymer is used as the second polymer. Therefore, the interactions between the inorganic particles and the first polymer can increase. Thus, the restructured hydrogel containing the inorganic particles can effectively achieve an enhancement of mechanical properties.

That is, the restructured hydrogel according to the present disclosure does not contain simply mixed and chaotically mixed first polymer and inorganic particle, but has a layered structure in which the inorganic particles and the first polymer are uniformly aligned and the inorganic particles are coated with the second polymer, and, thus, the first polymer and the inorganic particles having different properties can easily interact with (bond to) each other. Therefore, the restructured hydrogel containing the inorganic particles can effectively achieve an enhancement of mechanical properties.

According to an embodiment of the present disclosure, the second polymer may include a member selected from the group consisting of polyethylene (PE), polyvinyl chloride (PVC), polyvinylpyrrolidone (PVP), polypropylene (PP), polyacrylic acid (PAA), polyvinyl acetate (PVA), polystyrene (PS), polyurethane (PU) and combinations thereof, but may not be limited thereto.

Then, the hydrogel is unidirectionally shrunk and dehydrated (S200).

The hydrogel prepared in a plate shape is unidirectionally shrunk and dehydrated. Thus, the hydrogel decreases in percentage of water content and increases in density. Specifically, the unidirectionally shrunk and dehydrated hydrogel is changed to a thin sheet without containing water, and, thus, the density of the polymer increases.

According to an embodiment of the present disclosure, the shrinkage and dehydration may be performed at a temperature from 10° C. to 100° C., but may not be limited thereto.

The dehydration may be performed at a temperature from 15° C. to 60° C., and more specifically, the dehydration may be performed at a temperature from 20° C. to 40° C.

In the unidirectional shrinkage and dehydration, a three-dimensional gel having a top surface, a bottom surface and a side surface connecting the top surface and the bottom surface is shrunk and dehydrated in a Z-direction and the vertical height (thickness) of the gel decreases.

The top surface of the hydrogel is uniformly dehydrated through the unidirectional shrinkage and dehydration and the hydrogel decreases only in thickness (height). Further, within the hydrogel, the polymer network and the inorganic particles are horizontally oriented to form layered structure and the density of the polymer increases. Thus, the mechanical properties are enhanced.

FIG. 3 is an electron micrograph of the cross section of a hydrogel containing inorganic particles after unidirectional shrinkage and dehydration in preparing of a hydrogel according to an example of the present disclosure.

Referring to FIG. 3, it can be seen that inorganic particles are horizontally oriented to form layered structure. The inorganic particles form a horizontally uniform layered structure, which results in a more remarkable enhancement of mechanical properties than a structure in which the inorganic particles are chaotically arranged.

Thereafter, the dehydrated hydrogel is additionally cross-linked and restructured (S300).

According to an embodiment of the present disclosure, the additional cross-linking and rehydrating may be performed by impregnating the dehydrated hydrogel in a cross-linker solution, but may not be limited thereto.

In the rehydration, the shrunk and dehydrated hydrogel in the form of a thin sheet without containing water is impregnated in the cross-linker solution to absorb water and then hydrogelated again.

In the additional cross-linking, the dehydrated hydrogel is impregnated in the cross-linker solution and additional cross-links are formed within the dehydrated hydrogel by the action of the cross-linker contained in the cross-linker solution.

FIG. 4 is an image of a restructured hydrogel according to an example of the present disclosure. According to the method for preparing a restructured hydrogel, a hydrogel can be prepared in various thicknesses without being limited to the illustrated thickness.

FIG. 5 is an electron micrograph of the top surface of the hydrogel of FIG. 3 which has been additionally cross-linked and rehydrated then lyophilized.

Referring to FIG. 5, only the top surfaces of the inorganic particles aligned in a layered structure can be observed. Thus, it can be seen that a uniformly layered structure is formed through unidirectional shrinkage and dehydration and maintained even during the process of additional cross-linkage and rehydration.

FIG. 6 is a schematic diagram showing a method for preparing a hydrogel according to a comparative example of the present disclosure.

Specifically, the simple cross-linking and swelling in FIG. 6 means impregnating the hydrogel in the cross-linker solution without performing unidirectional shrinkage and dehydration, and by doing so, the added cross-links in the cross-linker solution result to additional cross-linking that absorbs water and expands in volume.

FIG. 7 is an electron micrograph of the top surface of the hydrogel prepared according to a comparative example of the present disclosure and which then has been lyophilized.

FIG. 7 shows the result of simple cross-linking and swelling as shown in FIG. 6 by impregnating the hydrogel in the cross-linker solution and performing simple cross-linking and expansion without performing unidirectional shrinkage and dehydration In reference to FIG. 7, if hydrogel that has not performed unidirectional shrinkage and dehydration is impregnated in cross-linker solution, the inorganic particles contained in the hydrogel are chaotically arranged; thus, various surfaces of the inorganic particles are observed.

Thus, it can be seen that only when the unidirectional shrinkage and dehydration is performed before the hydrogel is impregnated in the cross-linker solution, the components comprising the hydrogel are oriented and form layered-structure. Thus, the restructuring process should be conducted ideally to produce restructured hydrogel.

Through the cross-linking reaction, additional cross-linking may be performed on the hydrogel, which may cause a further enhancement of mechanical strength.

Further, the cross-linker solution contains a cross-linker. The cross-linker may include the same cross-linker as used in the process of forming the hydrogel, but may not be limited thereto.

According to an embodiment of the present disclosure, the cross-linker solution may contain an ion selected from the group consisting of $Ba^{2+}$, $Ca^{2+}$, $Al^{3+}$, $Fe^{3+}$, $Fe^{2+}$, $Mg^{2+}$, $Cu^{2+}$, $Sr^{2+}$, $Co^{2+}$, $Mn^{2+}$, $Ni^{2+}$, $Sn^{2+}$, $Zn^{2+}$, $Ga^{3+}$, $Ti^{3+}$, $Na^+$, $K^+$, $Li^+$ and combinations thereof, but may not be limited thereto.

According to an embodiment of the present disclosure, the cross-linker solution may contain a material selected from the group consisting of N,N"-methylenebisacrylamide (MBAA), N,N-dimethylacrylamide (DMA), glutaraldehyde (GA), N,N"-bis(acryloyl)cystamine (BAC), N,N"-diallyl tartar diamide (DATD), ethylene diacrylate (EDIA) and combinations thereof, but may not be limited thereto.

The cross-linker solution used during the additional cross-linking and rehydrating process may be ionic cross-linker and ideally includes the following: $LiCl$, $SrCl_2$, $NiCl_2$, $CaCl_2$, $BaCl_2$, $CaCl_2$, $AlCl_3$, $FeCl_3$. For example, as in the alginate in the first polymer, the ionic cross-linker can form additional ionic cross-link bonds and improve mechanical properties of the restructured hydrogel.

The mechanical properties can be regulated by regulating the kind or amount of the cross-linker. In this regard, as the first polymer contains the cross-linker at a higher ratio, the first polymer has a higher density. Therefore, the mechanical properties of the restructured hydrogel according to the present disclosure can be enhanced.

FIG. 8 is a photograph of a large-area hydrogel according to an example of the present disclosure.

Unlike in a conventional process for preparing a large-area material by performing drawing, twisting and weaving processes to enhance mechanical properties, the restructured hydrogel according to the present disclosure can be produced in large area through a simple process and the produced large-area hydrogel can be used by cutting into a desired size.

More specifically, the method to prepare restructured hydrogel according to the present disclosure is to place a hydrogel on a wide plate and then subject it to shrinkage, dehydration, additional cross-linking reaction, and rehydration; thus large-area hydrogel may be prepared through a simple process.

In addition, according to a second aspect of the present disclosure, there is provided a restructured hydrogel, including a restructured polymer network and inorganic particles, and the restructured polymer network is aligned unidirectionally, and the restructured polymer network and inorganic particles form a layered structure.

As for the restructured hydrogel from the second aspect of the present disclosure, detailed descriptions that are repeated in the first aspect of the present disclosure are removed. Even if these descriptions are removed, information provided in the first aspect of the present disclosure may be applied identical in the second aspect of the present disclosure.

Since the polymer network is aligned unidirectionally, the polymer network and the inorganic particles form a uniformly layered structure, and, thus, the resultant hydrogel has a higher density than a hydrogel having a structure in which inorganic particles are chaotically arranged and thus can be enhanced in mechanical properties.

FIG. 9 is a photograph of a hydrogel according to an example of the present disclosure.

The hydrogel has excellent mechanical properties and thus is not easily fractured by mechanical force. Therefore, the hydrogel can be easily changed to a desired shape.

The restructured hydrogel according to the present disclosure can be applied to a wide variety of fields due to the above-described features. For example, the restructured hydrogel according to the present disclosure can be variously applied to artificial muscles, artificial ligaments, artificial tendons, bioelectronic devices, gel-type electrolyte (separator) and the like.

In particular, the restructured hydrogel according to the present disclosure has rapidly enhanced mechanical strength, stiffness and fracture toughness compared with the conventional hydrogel and thus can also be used under the pressure of great load such as in muscles, tendons, and gel-type electrolyte (separator).

However, the effects discussed in the present disclosure are not limited thereof and there may be other effects to be presented by the present disclosure.

Furthermore, according to a third aspect of the present disclosure, there is provided a bioelectronic device containing a restructured hydrogel according to the second aspect of the present disclosure.

As for bioelectronic device from the third aspect of the present disclosure, detailed descriptions that are repeated in the second aspect of the present disclosure are removed. Even if these descriptions are removed, information provided in the second aspect of the present disclosure may be applied identical in the third aspect of the present disclosure.

The restructured hydrogel according to the present disclosure has rapidly enhanced mechanical strength, stiffness, and fracture toughness compared with that made by conventional technologies and thus can also be used in various bioelectric device materials. For example, as artificial human muscles or tendons of a living body that requires enhanced mechanical properties or as devices that interact effectively with the living body (stimulating or sensing) by attaching the electronic device on the artificial living body.

The above-described aspects are provided by way of illustration only and should not be construed as liming the present disclosure. Besides the above-described embodiments, there may be additional embodiments described in the accompanying drawings and the detailed description.

Hereinafter, the present disclosure will be described in more detail with reference to examples. The following examples are provided only for explanation, but do not intend to limit the scope of the present disclosure.

Example 1-1

A hydrogel (hydrogel composite) containing a first polymer formed of 2 wt % alginate (ALG) and 12 wt % polyacrylamide was prepared by mixing N,N''-methylenebisacrylamide (MBAA) in the amount of 0.08 wt % based on the amount of acrylamide (AM), tetramethylethylenediamine (TMEDA) in the amount of 0.28 wt % based on the amount of AM, ammonium persulfate (APS) in the amount of 4 wt % based on the amount of AM, and $CaSO_4$ in the amount of 15 wt % based on the amount of ALG in a solution containing ALG and AM, flattening the mixture by molding the mixture solution on a glass plate, and storing it for a day for complete cross-linking.

The hydrogel was shrunk and dehydrated unidirectionally (in a Z-direction) on a flat plate to obtain a thin sheet. Then, the restructure hydrogel was prepared by impregnating the dehydrated sheet in a cross-linker solution containing $BaCl_2$ so as to form additional cross-links with the ALG in the dehydrated sheet.

Example 1-2

The restructured hydrogel was prepared by the same method as in Example 1-1 except that inorganic plate-shaped alumina (alumina platelets) was added during the process of preparing the hydrogel. The weight of the Alu added was 0.5 times the weight of the first polymer.

Example 1-3

The restructured hydrogel was prepared by the same method as in Example 1-1 except that inorganic alumina platelets were added during the process of preparing the hydrogel. The weight of the alumina platelets added was 1.3 times the weight of the first polymer.

Example 1-4

The restructured hydrogel was prepared by the same method as in Example 1-1 except that inorganic alumina platelets were added during the process of preparing the hydrogel. The weight of the alumina platelets added was 2 times the weight of the first polymer.

Example 1-5

The restructured hydrogel was prepared by the same method as in Example 1-1 except that inorganic alumina platelets were added during the process of preparing the hydrogel. The weight of the alumina platelets added was 3.4 times the weight of the first polymer.

Example 2-1

The restructured hydrogel was prepared by the same method as in Example 1-1 except that the dehydrated hydrogel sheet was impregnated in a cross-linker solution containing $AlCl_3$.

Example 2-2

The restructured hydrogel was prepared by the same method as in Example 1-2 except that the dehydrated hydrogel sheet was impregnated in a cross-linker solution containing $AlCl_3$.

Example 2-3

The restructured hydrogel was prepared by the same method as in Example 1-3 except that the dehydrated hydrogel sheet was impregnated in a cross-linker solution containing $AlCl_3$.

Example 2-4

The restructured hydrogel was prepared by the same method as in Example 1-4 except that the dehydrated hydrogel sheet was impregnated in a cross-linker solution containing $AlCl_3$.

Example 2-5

The restructured hydrogel was prepared by the same method as in Example 1-5 except that the dehydrated hydrogel sheet was impregnated in a cross-linker solution containing $AlCl_3$.

Example 3-1

The restructured hydrogel was prepared by the same method as in Example 1-1 except that the dehydrated hydrogel sheet was impregnated in a cross-linker solution containing $FeCl_3$.

Example 3-2

The restructured hydrogel was prepared by the same method as in Example 1-2 except that the dehydrated hydrogel sheet was impregnated in a cross-linker solution containing $FeCl_3$.

Example 3-3

The restructured hydrogel was prepared by the same method as in Example 1-1 except during the preparation of hydrogel, the weight of the inorganic alumina platelets added was 0.8 times the weight of the first polymer and the dehydrated hydrogel sheet was impregnated in a cross-linker solution containing $FeCl_3$.

Example 3-4

The restructured hydrogel was prepared by the same method as in Example 1-3 except the dehydrated hydrogel sheet was impregnated in a cross-linker solution containing $FeCl_3$.

Example 3-5

The restructured hydrogel was prepared by the same method as in Example 1-4 except the dehydrated hydrogel sheet was impregnated in a cross-linker solution containing $FeCl_3$.

Example 3-6

The restructured hydrogel was prepared by the same method as in Example 1-5 except the dehydrated hydrogel sheet was impregnated in a cross-linker solution containing $FeCl_3$.

Comparative Example 1

The hydrogel was prepared by the same method as in Example 1-1 except that the step of unidirectional shrinkage and dehydration and the step of additional cross-linking and rehydration are omitted.

Comparative Example 2

The hydrogel was prepared by the same method as in Example 1-1 except that the step of unidirectional shrinkage and dehydration and the step of additional cross-linking and rehydration are omitted. The simple cross-linking and swelling process as in FIG. 6 were used.

Comparative Example 2-2

The hydrogel was prepared by the same method as in Comparative Example 2-1 except that inorganic alumina platelets were added during the process of preparing the hydrogel. The weight of the alumina platelets added was 0.5 times the weight of the first polymer.

Comparative Example 2-3

The hydrogel was prepared by the same method as in Comparative Example 2-1 except that inorganic alumina platelets were added during the process of preparing the hydrogel. The weight of the alumina platelets added was 1.3 times the weight of the first polymer.

Comparative Example 2-4

The hydrogel was prepared by the same method as in Comparative Example 2-1 except that inorganic alumina platelets were added during the process of preparing the hydrogel. The weight of the alumina platelets added was 2 times the weight of the first polymer.

Comparative Example 2-5

The hydrogel was prepared by the same method as in Comparative Example 2-1 except that inorganic alumina platelets were added during the process of preparing the hydrogel. The weight of the alumina platelets added was 3.4 times the weight of the first polymer.

Test Example 1

The hydrogels prepared according to Example 1-1 and Comparative Example 2-1 were hung in the air and fast-dried at 60° C. and then compared with each other in shape.

FIG. 10 is a photograph of the restructured hydrogel after fast-drying according to an example of the present disclosure.

FIG. 11 is a photograph of the hydrogel after fast-drying according to a comparative example of the present disclosure.

Referring to FIG. 10, as for the restructured hydrogel according to Example 1-1, unidirectional shrinkage and dehydration, along with additional cross-linking and rehydration were performed. During the fast-drying, no noticeable changes were observed. This is due to the increase in density as the polymer network within hydrogel is aligned.

Referring to FIG. 11, it can be seen that the polymer network from Comparative Example 2-1, in which only simple cross-linking and expansion was performed, is not aligned, has low density, and thus was twisted extensively during the fast-drying.

Therefore, it can be confirmed from Test Example 1, that the restructuring process (unidirectional shrinkage and dehydration, additional cross-linking and rehydration) aligns polymer network within the hydrogel and increases the density.

Test Example 2

A fast-drying test was conducted on the hydrogels of Example 1-4 and Comparative Example 2-4 by the same method as in Test Example 1, and then the microstructures of the hydrogels were compared using a microscope.

FIG. 12 shows a photograph of the restructured hydrogel containing inorganic particles according to an example of the present disclosure after the fast-drying and an electron micrograph of the cross section of the restructured hydrogel.

FIG. 13 shows a photograph of the hydrogel according to the comparative example of the present disclosure after fast-drying and an electron micrograph of the cross section of the hydrogel.

Referring to FIGS. 12 and 13, it can be confirmed that the hydrogel according to Comparative Example 2-4, in which the restructuring processes such as unidirectional shrinkage and dehydration along with additional cross-linking and rehydration were not performed, had relatively low polymer density and cross-link density, and contained chaotically arranged inorganic particles with a low degree of orientation, and thus was twisted extensively during the fast drying.

Test Example 3

The mechanical properties of the hydrogels of Example 1-1, Comparative Example 1, and Comparative Example 2-1 were compared with one another during a tension test.

FIG. 14 shows the test results of the mechanical properties in the tension test of the hydrogels according to Example and Comparative examples of the present disclosure.

Referring to FIG. 14, it can be confirmed that the hydrogel of Example 1-1, in which the restructuring process was performed, has the highest tensile strength, tensile elastic modulus, and fracture energy values.

In contrast, the hydrogel of Comparative Example 2-1, in which simple cross-linking and swelling was performed while the restructuring process was not performed, has higher mechanical properties compared to the hydrogel of Comparative Example 1, in which both the restructuring process and the simple cross-linking and swelling were not performed. However, the hydrogel of Comparative Example 2-1 has lower mechanical properties compared to the hydrogel of Example 1-1, in which the restructuring process was performed.

From the results of Test Example 3, it can be confirmed that, through unidirectional shrinkage and dehydration as well as additional cross-linking and rehydration as shown in FIG. 2, the hydrogel experiences restructuring process, where the structure is oriented, and thus the mechanical properties of the hydrogel are improved.

Test Example 4

The mechanical properties of the hydrogels of Example 1-1, Example 1-4, Comparative Example 2-1, and Comparative Example 2-4 were compared with one another.

FIG. 15 shows the test results of the mechanical properties of the hydrogels according to an example and a comparative example of the present disclosure.

FIG. 16 shows the test results of the mechanical properties of the hydrogel according to an example and a comparative example of the present disclosure.

Referring to FIG. 16, it can be confirmed that the hydrogels produced in Comparative Example 2-1 and Comparative Example 2-4, where no restructuring process as in FIG. 2 was performed and instead the hydrogels were impregnated in the cross-linker $BaCl_2$, and then the simple cross-linking and expansion were performed as in FIG. 6, do not show significant increase in the mechanical properties when inorganic particles are added.

Therefore, through the restructuring process, the polymer network and the inorganic particles of the restructured hydrogel orient horizontally, form layered structure, and the density of the hydrogel increases. Additionally, interactions among inorganic particles increase, and thus the mechanical properties of hydrogel are effectively enhanced.

Furthermore, from the test results of Example 1-1 and Example 1-4, the hydrogel of Example 1-4, in which inorganic particles have been added, has higher tensile strength, elastic modulus, and tensile modulus than those of the hydrogel of Example 1-1. Accordingly, the amount of inorganic particles added affect tensile strength, elastic modulus, and the tensile modulus of the hydrogel.

Test Example 5

Various hydrogels prepared from various restructuring processes using different ionic cross-linkers and adding different amounts of the inorganic particles according to Examples (1-1, 1,2, 1-3, 1-4, 1-5, 2-1, 2-2, 2-3, 2-4, 2-5, 3-1, 3-2, 3-3, 3-4, 3-5 and 3-6) were compared with one another in terms of the mechanical properties.

FIG. 17 shows the test results of the mechanical properties of the hydrogels according to various examples of the present disclosure.

FIG. 18 shows the test results of the mechanical properties of the hydrogels according to various examples of the present disclosure.

Referring to FIGS. 17 and 18, it can be confirmed that variety of hydrogels can be prepared to have various ranges of mechanical properties depending on a kind of the cross-linker included in the cross-linker solution, which is used for additional cross-linking and rehydrating during the restructuring process.

Furthermore, it can be confirmed that, even when various cross-linkers are used, the tensile strength, the elastic modulus, and the tensile modulus of the hydrogel can be conveniently regulated depending on the amount of inorganic particles. Also, it can be confirmed that a variety of hydrogels can be prepared to have various mechanical properties by regulating a kind of the cross-linker and the amount of the inorganic particles.

While specific examples have been shown and described above, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for preparing a restructured hydrogel, comprising:
    forming a hydrogel comprising a first polymer;
    unidirectionally shrinking and dehydrating the hydrogel; and
    additionally cross-linking and rehydrating the dehydrated hydrogel,
    wherein the first polymer comprises at least one selected from the group consisting of alginate (ALG), polyethylene glycol (PEG), chitosan, gelatin, polyacrylic acid (PAA), polyacrylamide (PAM), polyNIPAM (PNIPAM), agar, poly(2-acrylamido-2-methylpropane sulfonic acid) (PAM PS) and combinations thereof; and
    the additional cross-linking and rehydrating are performed by impregnating the dehydrated hydrogel in a cross-linker solution.

2. The method for preparing a restructured hydrogel of claim 1,
    wherein the first polymer is formed through cross-linking by ionic bonds and/or covalent bonds.

3. The method for preparing a restructured hydrogel of claim 1,
    wherein the cross-linker solution comprises an ion selected from the group consisting of $Ba^{2+}$, $Ca^{2+}$, $Al^{3+}$, $Fe^{2+}$, $Fe^{3+}$, $Mg^{2+}$, $Cu^{2+}$, $Sr^{2+}$, $Co^{2+}$, $Mn^{2+}$, $Ni^{2+}$, $Sn^{2+}$, $Zn^{2+}$, $Ga^{3+}$, $Ti^{3+}$, $Na^+$, $K^+$, $Li^+$ and combinations thereof.

4. The method for preparing a restructured hydrogel of claim 1,
    wherein the cross-linker solution comprises a material selected from the group consisting of N,N"-methylenebisacrylamide (MBAA), N,N-dimethylacrylamide (DMA), glutaraldehyde (GA), N,N"-bis(acryloyl)cystamine (BAC), N,N"-diallyl tartar diamide (DATD), ethylene diacrylate (EDIA) and combinations thereof.

5. The method for preparing a restructured hydrogel of claim 1,
wherein the forming of the hydrogel comprises:
hydrogelating a mixture solution by adding a cross-linker to a monomer of the first polymer.

6. The method for preparing a restructured hydrogel of claim 5,
wherein the mixture solution further comprises inorganic particles.

7. The method for preparing a restructured hydrogel of claim 6,
wherein the inorganic particles comprise a member selected from the group consisting of aluminum oxide ($Al_2O_3$), boron nitride (BN), mica, illite, magnesium hydroxide ($Mg(OH)_2$), aluminum nitride (AlN), boron carbide ($B_4C$) and combinations thereof.

8. The method for preparing a restructured hydrogel of claim 6,
wherein the first polymer and the inorganic particles form a layered structure.

9. The method for preparing a restructured hydrogel of claim 6,
wherein the inorganic particles are coated with a second polymer.

10. The method for preparing a restructured hydrogel of claim 9,
wherein the second polymer comprises a member selected from the group consisting of polyethylene (PE), polyvinyl chloride (PVC), polypropylene (PP), polyvinylpyrrolidone (PVP), polyacrylic acid (PAA), polyvinyl acetate (PVA), polystyrene (PS), polyurethane (PU) and combinations thereof.

11. The method for preparing a restructured hydrogel of claim 1,
wherein the shrinkage and dehydration are performed at a temperature from 10° C. to 100° C.

12. A restructured hydrogel, comprising:
a restructured polymer network; and
inorganic particles,
wherein the restructured polymer network comprises a network of a first polymer aligned unidirectionally and restructured by being cross-linked while in aligned state, the inorganic particles being dispersed in the network of the first polymer, and
the restructured polymer network and the inorganic particles form a layered structure; and
wherein the first polymer comprises at least one selected from the group consisting of alginate (ALG), polyethylene glycol (PEG), chitosan, gelatin, polyacrylic acid (PAA), polyacrylamide (PAM), polyNIPAM (PNIPAM), agar, poly(2-acrylamido-2-methylpropane sulfonic acid) (PAMPS) and combinations thereof, and
the cross-linking is performed by impregnating a unidirectionally shrunk and dehydrated hydrogel comprising the first polymer with a cross-linker solution.

13. A bioelectronic device comprising a restructured hydrogel of claim 12.

14. The restructured hydrogel of claim 12,
wherein the inorganic particles are coated with a second polymer, the second polymer comprising at least one member selected from the group consisting of polyethylene (PE), polyvinyl chloride (PVC), polypropylene (PP), polyvinylpyrrolidone (PVP), polyacrylic acid (PAA), polyvinyl acetate (PVA), polystyrene (PS), polyurethane (PU) and combinations thereof.

15. A method for preparing a restructured hydrogel, comprising:
forming a hydrogel composite comprising a first polymer and a second polymer;
unidirectionally shrinking and dehydrating the hydrogel composite into a sheet;
additionally cross-linking the hydrogel by impregnating the dehydrated hydrogel with a cross-linker solution; and
rehydrating the hydrogel composite,
wherein the first polymer comprises at least one selected from the group consisting of alginate (ALG), polyethylene glycol (PEG), chitosan, gelatin, polyacrylic acid (PAA), polyacrylamide (PAM), polyNIPAM (PNIPAM), agar, poly(2-acrylamido-2-methylpropane sulfonic acid) (PAMPS) and combinations thereof.

16. The method for preparing a restructured hydrogel of claim 15,
wherein the cross-linker solution comprises an ion selected from the group consisting of $Ba^{2+}$, $Ca^{2+}$, $Al^{3+}$, $Fe^{2+}$, $Fe^{3+}$, $Mg^{2+}$, $Cu^{2+}$, $Sr^{2+}$, $Co^{2+}$, $Mn^{2+}$, $Ni^{2+}$, $Sn^{2+}$, $Zn^{2+}$, $Ga^{3+}$, $Ti^{3+}$, $Na^+$, $K^+$, $Li^+$ and combinations thereof.

* * * * *